United States Patent [19]

Saccomano et al.

[11] Patent Number: 5,037,846

[45] Date of Patent: Aug. 6, 1991

[54] INDOLYL-3 POLYAMINES AND THEIR USE AS ANTAGONISTS OF EXCITATORY AMINO ACID NEUROTRANSMITTERS

[75] Inventors: Nicholas A. Saccomano, Ledyard; Robert A. Volkmann, Mystic, both of Conn.

[73] Assignee: Pfizer Inc., New York, N.Y.

[21] Appl. No.: 560,699

[22] Filed: Jul. 31, 1990

Related U.S. Application Data

[63] Continuation-in-part of Ser. No. 460,207, Jan. 2, 1990, abandoned.

[51] Int. Cl.$^5$ .................. C07D 209/12; A61K 31/415
[52] U.S. Cl. ...................................... 514/419; 548/495
[58] Field of Search ........................ 514/419; 548/495

[56] References Cited

U.S. PATENT DOCUMENTS 4,925,664 5/1990 Jackson et al. ..................... 424/537
4,950,739 8/1990 Cherksey et al. .................. 530/350

FOREIGN PATENT DOCUMENTS 8907608 8/1989 PCT Int'l Appl. .

*Primary Examiner*—David B. Springer
*Attorney, Agent, or Firm*—Peter C. Richardson; J. Trevor Lumb; D. Stuart McFarlin

[57] ABSTRACT

This invention relates to certain polyamines found to be present in the venom of the *Agelenopsis aperta* spider. The polyamines of this invention and the salts thereof antagonize excitatory amino acid neurotransmitters, which neurotransmitters affect cells of various organisms, and are useful in antagonizing said neurotransmitters, per se, in the treatment of excitatory amino acid neurotransmitter mediated diseases and conditions and in the control of invertebrate pests. This invention also relates to compositions comprising said polyamines and salts thereof.

21 Claims, No Drawings

INDOLYL-3 POLYAMINES AND THEIR USE AS ANTAGONISTS OF EXCITATORY AMINO ACID NEUROTRANSMITTERS

CROSS REFERENCE TO RELATED APPLICATION

This is a continuation-in-part of application Ser. No. 07/460,207, filed Jan. 2, 1990 abandoned.

BACKGROUND OF THE INVENTION

1. Field of the Invention

This invention relates to certain polyamines found to be present in the venom of the *Agelenopsis aperta* spider. The polyamines and the pharmaceutically-acceptable salts thereof are antagonists of excitatory amino acid neurotransmitters which neurotransmitters affect cells including neuronal cells of a variety of organisms including invertebrates and vertebrates. This invention also relates to the use of such polyamines and their salts in antagonizing excitatory amino acid neurotransmitters which neurotransmitters affect cells such as cells in the nervous system of an organism, per se, in the treatment of excitatory amino acid neurotransmitter mediated diseases and conditions in a mammal and control of invertebrate pests, and to compositions comprising said polyamines and salts thereof.

2. Background of the Invention

It has been reported that the venom of the spider *Agelenopsis aperta* contains at least two toxins which affect calcium currents Jackson, H., et al., Soc. Neu. Sci. Abstr. 12:1078 (1987). Those authors disclose a toxin, referred to therein as AG2, which has a molecular weight of less than 1,000 daltons and appears to suppress calcium currents in a broad range of tissues Further, Jackson, H., et al., Soc. Neu. Sci. Abstr. 12:730 (1986) report another toxin from *Agelenopsis aperta* comprising a component of about 6,000 M.W. That toxin is reported to effect presynaptic blockade of transmission and it has been suggested that the toxin blocks calcium channels associated with the release of neurotransmitter.

Certain polyamines found to be present in the venom of the *Agelenopsis aperta* spider are disclosed in U.S. patent application Ser. No. 07/346,181, filed Apr. 28, 1989 and assigned to the assignees hereof. Those polyamines and the pharmaceutically-acceptable salts thereof are disclosed therein as blockers of excitatory amino acid receptors in cells and one such polyamine, $B_1$ therein, is also disclosed as a blocker of calcium channels in cells. Those polyamines are described therein as follows:

AGEL 452:

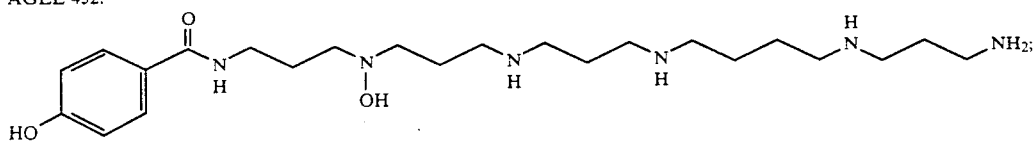

AGEL 468:

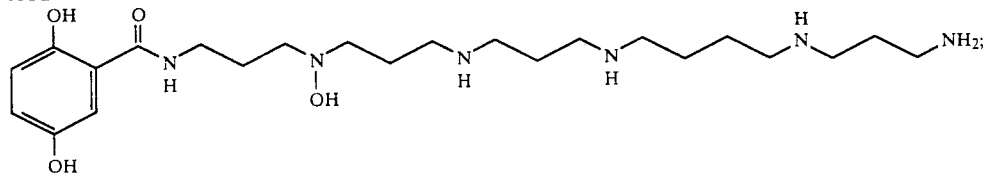

AGEL 448:

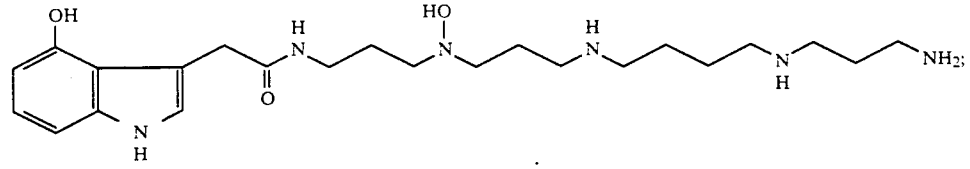

AGEL 505:

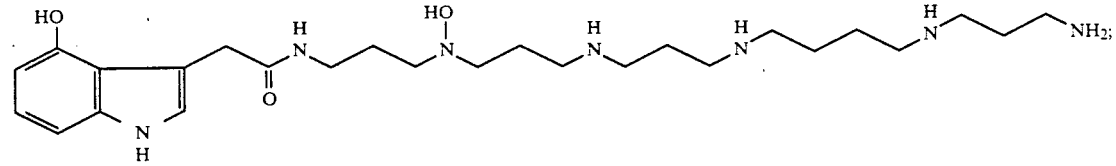

AGEL 489:

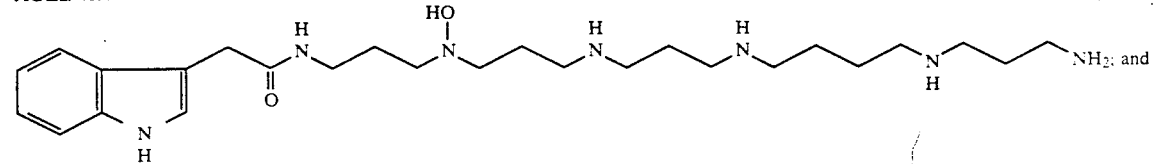

AGEL 504:
a compound having the following identifying characteristics:

(a) present in a fraction from crude venom of the *Agelenopsis aperta* spider which elutes off a C-18 Vydac® 22 mm×250 mm, 300 Å pore size, 10 μ particle size column using a flow rate of 15 ml/min. and a solvent system using a linear gradient program of 5% → 20% B, 95% → 80% A [0 → 30 min.] then 20% → 70% B, 80% → 30% A [30 → 55 min.], where A is 0.1% aqueous TFA and B is acetonitrile, at about 22.75 minutes;

(b) present in a fraction of the fraction described in (a), above, which elutes off a C-18 Vydac® 22 mm×250 pore size, 300 Å pore size, 10 μ particle size column using a flow rate of 15 ml/min. and a solvent system using a non-linear gradient program of 0% → 0% B, 100% → 100% A [0 → 5 min.], then 0% → 10% B, 100% → 90% A [5 → 20 min.] (Waters curve 1) then 10% → 20% B, 90% → 80% A [20 → 30 min.] (Waters curve 6) then 20% → 50% B, 80% → 50% A [30 → 40 min.](Waters curve 11), where A is 0.1% aqueous TFA and B is acetonitrile, at about 21.5 minutes; and (c) FAB MS: high resolution 505.3861 calculated for $C_{27}H_{48}N_6O_3$.

Compounds which are excitatory amino acid neurotransmitter antagonists have a variety of utilities. Excitatory amino acid neurotransmitter antagonists can find clinical application in the treatment of such conditions as stroke, cerebral ischemia, neuronal degeneration disorders such as Alzheimer's disease and epilepsy and as psychotherapeutants, among others. See *Excitatory Amino Acids in Health and Disease*, D. Lodge, Ed., John Wiley and Sons Ltd., New York, N.Y. 1988, the teachings of which are incorporated herein by reference. Further, such compounds are useful in the study of the physiology of cells such as neuronal cells and in the control of invertebrate pests.

SUMMARY OF THE INVENTION

This invention concerns certain polyamines found to be present in the venom of the *Agelenopsis aperta* spider. The polyamines of this invention are as follows:

AGEL 416:
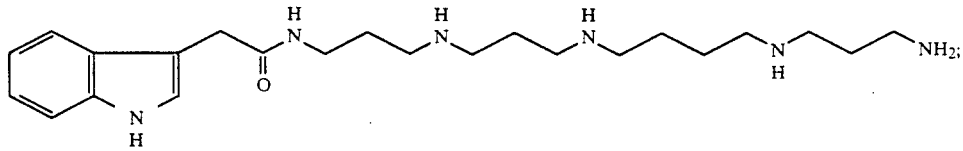

AGEL 464:
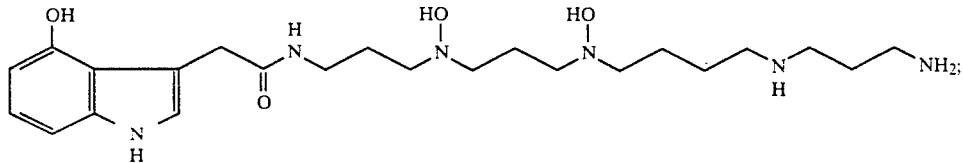

AGEL 489(A):
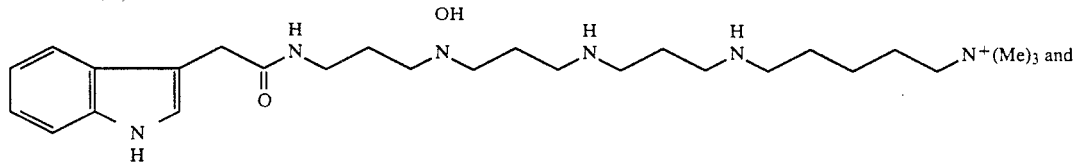

AGEL 521:
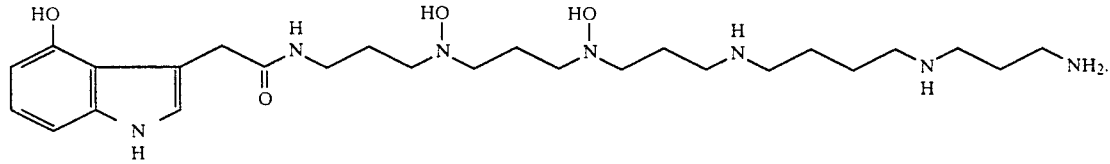

The polyamines of this invention and the pharmaceutically-acceptable salts thereof are antagonists of excitatory amino acid neurotransmitters which neurotransmitters affect cells. Thus, said polyamines are useful in antagonizing such excitatory amino acid neurotransmitters, per se. The polyamines of this invention are also useful in the control of invertebrate pests and in the treatment of diseases and conditions in a mammal mediated by excitatory amino acid neurotransmitters. Said polyamines are useful, also, as psychotherapeutants for a mammal.

This invention also concerns pharmaceutical compositions comprising said polyamines and methods of administering said polyamines.

DETAILED DESCRIPTION OF THE INVENTION

Venom is obtained from the *Agelenopsis aperta* spider through the process of milking by electrical stimulation according to standard methods well known to those skilled in the art. It is preferred that the method employed is one which safeguards against contamination of the whole venom by abdominal regurgitant or hemolymph. Such methods are well known to those skilled in the art. The whole venom so obtained is stored in a frozen state at about −78° C. until used for purification as described below.

Purification of the constituents from the whole venom is accomplished by reverse phase high performance liquid chromatography (HPLC) on a variety of preparative and semi-preparative columns such as C-4 and C-18 Vydac® columns (Rainin Instrument Co.

Inc., Mack Road, Woburn Mass. 01801), C-18 Baker columns (J. T. Baker Inc., 22 Red School Lane, Phillipsburg, N.J. 08865) and Dynamax Phenyl columns (Rainin Instrument Co. Inc., Mack Road, Woburn, Mass. 01801). Peak detection is carried out monochromatically at 220-230 nm. Further analysis of the fractions can be accomplished with, for example, polychrome UV data collected with a Waters 990 diode array detector (Millipore Corporation, Waters Chromatography Division, 34 Maple Street, Milford, Mass. 01757). The fractions from the columns are collected by known methods such as through the use of an ISCO/'FOXY" fraction collector and an ISCO 2159 peak detector (ISCO, 4700 Superior, Lincoln, Nebr. 68504). The fractions are collected in appropriately sized vessels such as sterile polyethylene laboratoryware. Concentration of the fractions is then accomplished by lyophilization from the eluant followed by lyophilization from water. Purity of the resulting constituent fractions then can be determined by chromatographic analysis using an analytical column with a gradient system which is more isocratic than the system used in the final purification of the fractions.

is 0.1% aqueous trifluoroacetic acid (TFA) and B is acetonitrile. The fractions are collected as described above. Six fractions so obtained, labeled 1, 2, 3, 4, 5, and 6 herein, were chosen for further analysis and/or purification. Another method for fractionation of whole venom comprises a C-18 Baker (4.6 mm×250 mm, 100 Å pore size, 5 μ particle size) column which is eluted using a flow rate of 1 ml/min. and isocratic conditions of 8% B, 92% A where A and B are as described above. However, for purposes of this invention, use of the C-18 Vydac® column and procedure described above is preferred for initial fractionation of whole venom.

Fractions 1, 2 and 3 were found to comprise polyamines which are described in U.S. application Ser. No. 07/346,181 and form no part of this invention. Fractions 4, 5 and 6 are subjected to further purification using various columns and conditions. The specifics for each subfractionation and the results thereof are given in Examples 2, 3 and 4 below.

As shown in the following Examples, the polyamine compounds which are comprised by fractions AGEL 416, AGEL 464, AGEL 489(A) and AGEL 521 are as follows:

AGEL 416:

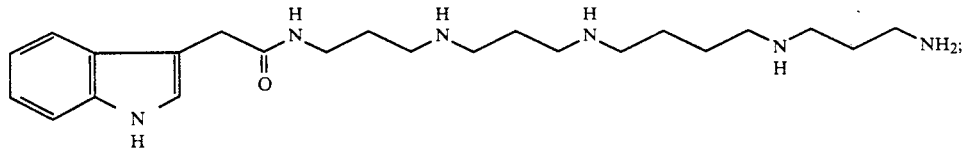

AGEL 464:

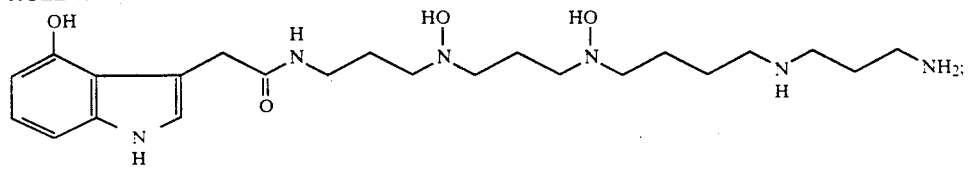

AGEL 489(A):

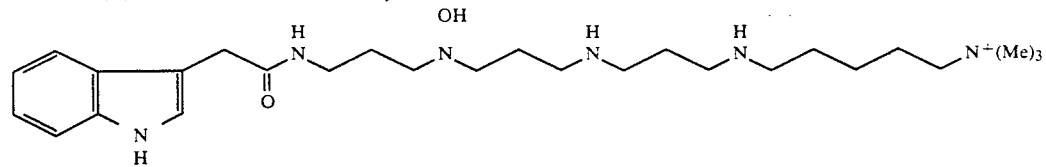

AGEL 521:

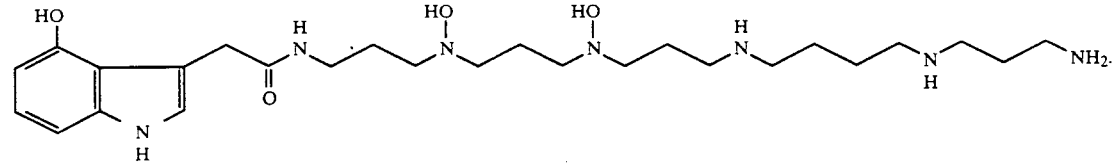

The structures comprised by the respective fractions are determined according to known analytical methods such as by mass spectrometry and nuclear magnetic resonance.

In practicing this invention and employing the general procedure outlined above, it has been found that a suitable column for initial fractionation of the venom is a C-18 Vydac® 22 mm×250 mm, 300 Å pore size, 10 μ particle size column. That column is eluted at a flow rate of 15 ml/min. using a linear gradient program of 100% → 80% A, 0% → 20% B [0 → 30 min.] where A Given the benefit of the disclosure herein with respect to the compounds present in fractions AGEL 416, AGEL 464, AGEL 489 (A) and AGEL 521, it is now possible to obtain said compounds by methods other than through isolation/purification from whole venom of *Agelenopsis aperta*. All such methods are within the scope of this invention. For example, the polyamine compounds of this invention can be made directly by synthetic methods.

A synthetic scheme for production of the polyamine of this invention of the formula

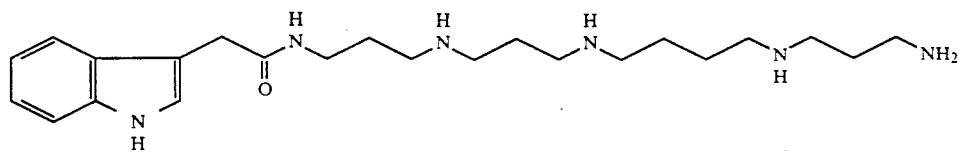
is shown in Reaction Schemes A to C, below.
REACTION SCHEME A
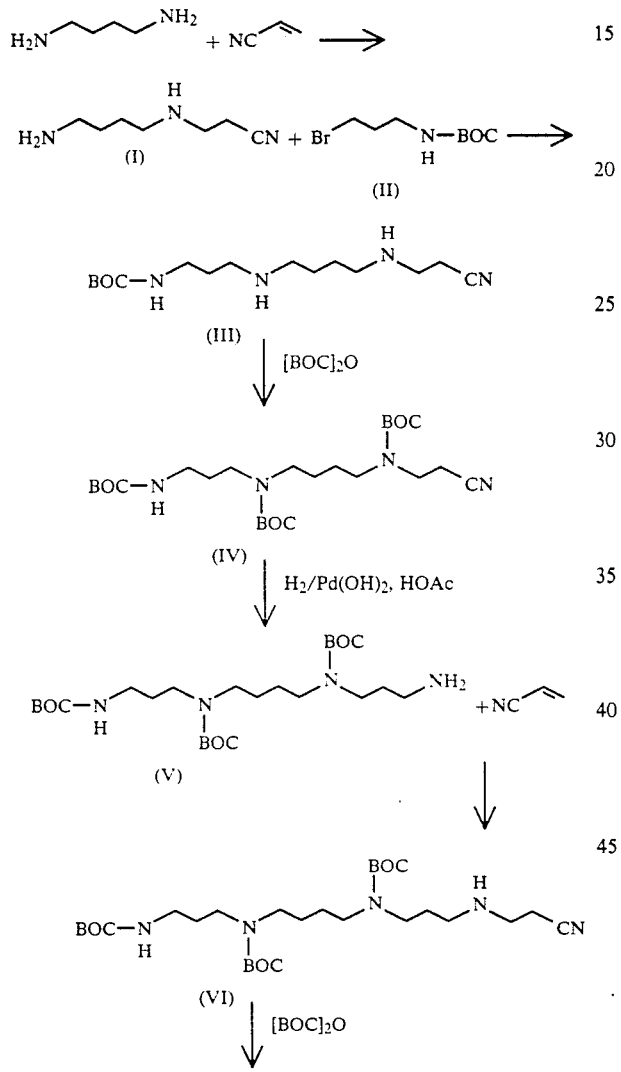
-continued
REACTION SCHEME A
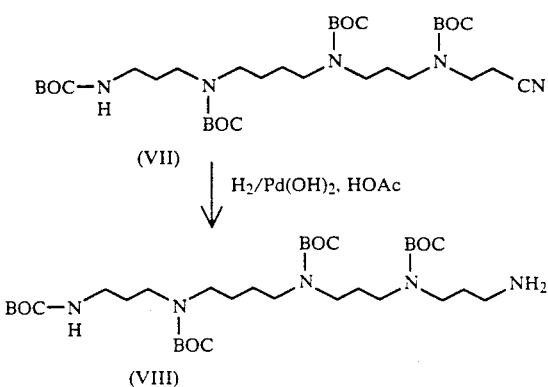
REACTION SCHEME B
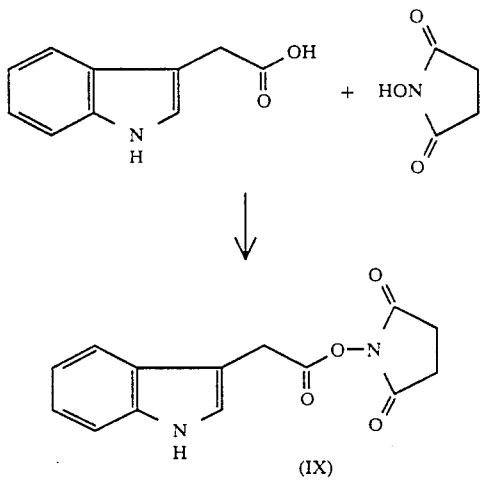
REACTION SCHEME C
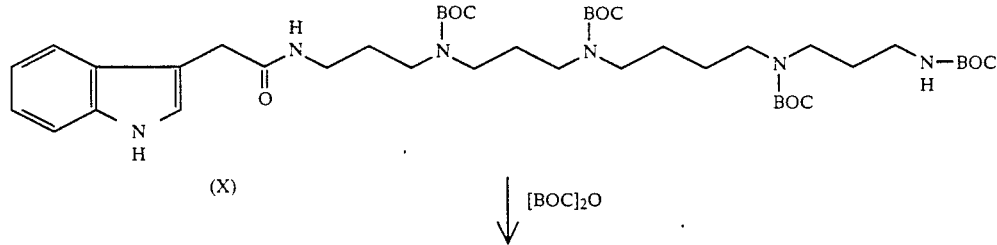

-continued
REACTION SCHEME C

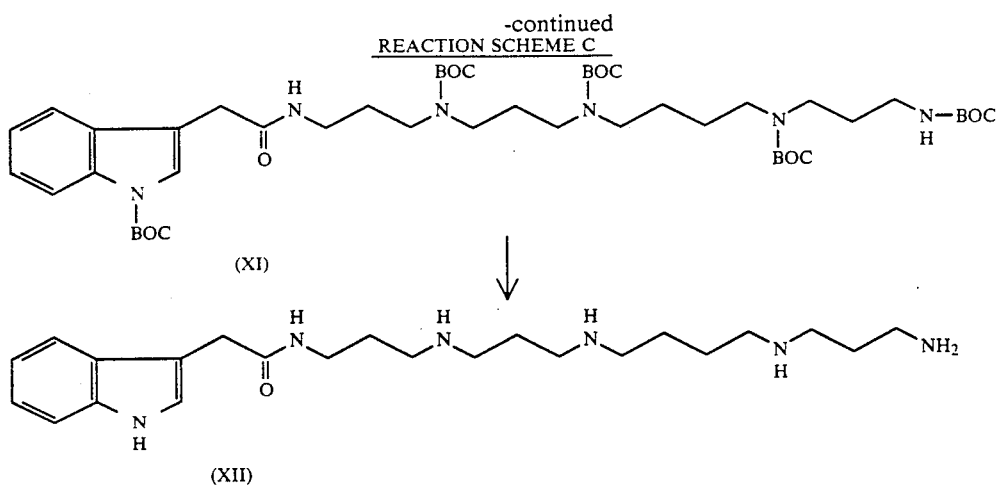

According to Reaction Scheme A, the polyamine intermediate compound of formula IV is prepared through a sequence of steps beginning with diaminobutane. Reaction conditions suitable to prepare the intermediate compound of formula VIII according to Reaction Scheme A are given in Example 5, parts A to G. Reaction Scheme B illustrates a method for the preparation of the intermediate compound of formula IX. Reaction conditions suitable to prepare that intermediate according to Reaction Scheme B are given in Example 5, part H. Preparation of the polyamine compound of this invention of the formula XII is shown in Reaction Scheme C. Reaction conditions suitable for the coupling of the intermediate compounds of formulae VIII and IX and the subsequent preparation of the compound of formula XII are given in Example 5, parts I to K.

The polyamines of this invention reversibly antagonize excitatory amino acid neurotransmitters, which neurotransmitters affect cells such as cells in the nervous system of a variety of organisms including invertebrates and vertebrates. The term vertebrates as used throughout is meant to include mammals. The term invertebrates as used throughout is meant to include, for example, insects, ectoparasites and endoparasites.

The ability of the polyamines of the present invention to antagonize excitatory amino acid neurotransmitters is demonstrated by their ability to block N-methyl-D-aspartic acid-induced (NMDA) elevations of cGMP in neonatal rat cerebellums according to the following procedure. Cerebellums from ten 8-14 day old Wistar rats are quickly excised and placed in 4° C. Krebs/bicarbonate buffer, pH 7.4 and then chopped in 0.5 mm×0.5 mm sections using a McIlwain tissue chopper (The Nickle Laboratory Engineering Co., Gomshall, Surrey, England). The resulting pieces of cerebellum are transferred to 100 ml of Krebs/bicarbonate buffer at 37° C. which is continuously equilibrated with 95:5 $O_2/CO_2$. The pieces of cerebellum are incubated in such a manner for ninety minutes with three changes of the buffer. The buffer then is decanted, the tissue centrifuged (1 min., 3200 r.p.m.) and the tissue resuspended in 20 ml of the Krebs/bicarbonate buffer. Then, 250 µl aliquots (approximately 2 mg) are removed and placed in 1.5 ml microfuge tubes. To those tubes are added 10 µl of the compound under study from a stock solution followed by 10 µl of a 2.5 mM solution of NMDA to start the reaction. The final NMDA concentration is 100 µM. Controls do not have NMDA added. The tubes are incubated for one minute at 37° C. in a shaking water bath and then 750 µl of a 50 mM Tris-Cl, 5mM EDTA solution is added to stop the reaction. The tubes are placed immediately in a boiling water bath for five minutes. The contents of each tube then are sonicated for 15 seconds using a probe sonicator set at power level three. Ten microliters are removed and the protein determined by the method of Lowry, Anal. Biochem. 100:201-220 (1979). The tubes are then centrifuged (5 min., 10,000 xg), 100 µl of the supernatant is removed and the level of cyclic GMP (cGMP) is assayed using a New England Nuclear (Boston, Mass.) cGMP RIA assay according to the method of the supplier. The data is reported as pmole cGMP generated per mg. protein.

Further, the ability of the polyamines of the present invention to antagonize excitatory amino acid neurotransmitters is demonstrated by their ability to block NMDA/glycine induced increases in cytosolic free $[Ca^{+2}]_i$ in dissociated cerebellar granule cells according to the following procedure. Cerebellar granule cells are prepared from the cerebellum of 8 day old rats (Wilkin, G. P. et al., Brain Res:115: 181-199, 1976). Squares (1 $cm^2$) of Aclar (proplastics Inc., 5033 Industrial Ave., Wall, N.J., 07719) are coated with poly-L-lysine and placed in 12-well dishes that contain 1 ml of Eagles Basal Medium. The cells are dissociated and aliquots containing $6.25 \times 10^6$ cells are added to each well containing the squares of Aclar. Cytosine-beta-D-arabino furanoside (final concentration 10 µM) is added 24 hours post plating. The cells are used for fura2 analysis at 6, 7 and 8 days of culture. The cells (attached to the Aclar squares) are transferred to 12-well dishes containing 1 ml of 2 µM fura2/AM (Molecular Probes Inc., Eugene, Oreg., 97402) in HEPES buffer (containing 0.1% bovine serum albumin, 0.1% dextrose, pH 7.4, magnesium-free). The cells are incubated for 40 minutes at 37° C.; the fura2/AM containing buffer is removed and replaced with 1 ml of the same buffer without fura2/AM. To a quartz cuvette is added 2.0 ml of prewarmed (37° C.) buffer. The cells on the Aclar are placed in the cuvette and the cuvette is inserted in a thermostated (37° C) holder equipped with a magnetic stirrer and the fluorescence is measured with a fluorescence spectrophotometer (Biomedical Instrument Group, University of Pennsylvania). The fluorescence signal is allowed to stabilize for about two minutes.

An increase in cytosolic free calcium, represented by an increase in fluorescence, is produced by the addition of 50 μM NMDA and 1 μM glycine. Then 5-20 μl of a stock solution of the compound under study in phosphate-buffered saline (PBS, pH 7.4) at appropriate concentrations are added to the cuvette. Calibration of the fluorescent signals and fura2/AM leakage correction are performed using the established procedures of Grynkiewicz, G. et al., J. Biol. Chem. 260:3440 (1985). At the completion of each test, the maximum fluorescence value (Fmax) is determined by addition of ionomycin (35 μM) and the minimum fluorescence value (Fmin) is determined by the subsequent addition of EGTA (12 mM) to chelate calcium. Employing the foregoing procedure, the ability of a subject compound to antagonize excitatory amino acid neurotransmitters is shown to occur by a decrease in fluorescence upon addition of the subject compound.

The polyamines of this invention are useful in antagonizing excitatory amino acid neurotransmitters, per se. As such, the polyamines are also useful in the control of invertebrate pests and in the treatment of excitatory amino acid neurotransmitter-mediated diseases and conditions in a mammal such as stroke, cerebral ischemia, neuronal degenerative disorders such as Alzheimer's disease and epilepsy. Said polyamines also are useful as psychotherapeutants in a mammal. Further, the polyamines are useful in the study of the physiology of cells including, but not limited to, cells of the nervous system.

Also within the scope of this invention are the pharmaceutically-acceptable salts of the polyamines of this invention. Such salts are formed by methods well known to those skilled in the art. For example, acid addition salts of the polyamines can be prepared according to conventional methods. Acid addition salts of the polyamines such as hydrochloric and trifluoroacetic acid addition salts thereof are preferred. Hydrochloric acid addition salts of the polyamines are particularly preferred.

When a polyamine or a pharmaceutically-acceptable salt thereof of this invention is to be administered to a mammal, it can be administered alone or in combination with pharmaceutically-acceptable carriers or diluents in a pharmaceutical composition according to standard pharmaceutical practice. The polyamines or pharmaceutically-acceptable salts thereof can be administered orally or parenterally. Parenteral administration includes intravenous, intramuscular, intraperitoneal, subcutaneous and topical administration.

For oral use of a polyamine or a pharmaceutically-acceptable salt thereof of this invention, the compound can be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents are lactose and dried corn starch. When aqueous suspensions are required for oral use, the active ingredient is combined with emulsifying and suspending agents. If desired, certain sweetening and/or flavoring agents can be added.

For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled to render the preparation isotonic.

When a polyamine or salt thereof of this invention is used in a human subject, the daily dosage will normally be determined by the prescribing physician. However, suitable dosages for the polyamines of this invention are from about 3 to 30 mg/kg/day. Moreover, the dosage will vary according to the age, weight and response of the individual patient, as well as the severity of the patient's symptoms and the potency of the particular compound being administered. Therefore, dosages outside the range given above are possible and are within the scope of this invention.

When a polyamine or salt thereof of this invention is used in control of invertebrate pests, said compound is administered to said invertebrate directly or provided to the environment of said invertebrate. For example, a compound of this invention can be sprayed as a solution onto said invertebrate. The amount of compound necessary for control of said invertebrate will vary according to the invertebrate and environmental conditions and will be determined by the person applying the compound.

When a polyamine or salt thereof of this invention is used in the physiological study of cells, said compound is administered to the cells according to methods well known to those skilled in the art. For example, said compound can be administered to cells in an appropriate physiological buffer. An appropriate concentration of the compounds of this invention for use in such studies is 100 μM. However, the concentration of said compounds in such studies may be greater than or much less than 100 μM. The amount of the compound administered will be determined by the person skilled in the art according to well known methods.

EXAMPLE 1

Initial fractionation of whole venom of *Agelenopsis aperta*

Whole venom of *Agelenopsis aperta*, obtained from Natural Product Sciences, Inc., Salt Lake City, Utah 84108 and which had been stored in the frozen state at about −78° C, was thawed, and 10 to 60 μl amounts thereof were diluted to 200 μl and loaded onto a C-18 Vydac ® (22 mm × 250 mm, 300 Å pore size, 10 μ particle size) column and eluted using a flow rate of 15 ml/min. and a solvent system using a linear gradient program of 0% → 20% B, 100% → 80% A [0 → 30 min.] where A is 0.1% aqueous trifluoroacetic acid (TFA) and B is acetonitrile. Peak detection was carried out monochromatically at 220 nm and fractions were collected with an ISCO/"FOXY" fraction collector and an ISCO 2159 peak detector. Fractions were collected from 0 minutes to 30 minutes. Based upon peak detection, the following fractions, among others, were collected:

| Fraction | Elution Time |
| --- | --- |
| 1 | about 13.8 min. |
| 2 | about 19.25 min. |
| 3 | about 21.0 min. |
| 4 | about 22.3 min. |
| 5 | about 23.1 min. |
| 6 | about 26.0 min. |

Fraction 1 was subfractionated using the same column and conditions as described above but with a Waters 990 diode array detector and it was found that Fraction 1 comprised the polyamine AGEL 452. That polyamine is described in pending U.S. application Ser. No. 07/346,181 and forms no part of this invention. Fraction 2 was as described for subfractionation of Fraction 1 and it was found that Fraction 2 comprised the polyamines AGEL 448 and AGEL 468, both of which are also described in said U.S. application Ser. No. 07/346,181. Neither of those polyamines form any part of this invention. Further, Fraction 3 was subfractionated using a C-4 Vydac ® (22 mm×250 mm, 300 Å pore size, 10 µ particle size) column using a linear gradient of 5% → 10% B, 95% → 90% A [0 → 30 min.] where A and B are as described above and a Waters 990 diode array detector. It was found that Fraction 2 comprised the polyamines 504 and 505 which are also described in U.S. application Ser. No. 07/346,181 and which form no part of the instant application.

EXAMPLE 2

Subfractionation of fraction 4 and determination of the structure therein

Fraction 4, obtained as described in Example 1, was loaded onto a C-18 Baker (4.6 mm×250 mm, 300 Å pore size, 5 µ particle size) column and eluted using a flow rate of 1 ml/min. and isocratic conditions of 8% B, 92% A where A and B are as defined in Example 1. Peak detection was accomplished using a Waters 990 diode array detector (λ=220 nm) and fraction collection was accomplished as described in Example 1. A subfraction, herein labelled AGEL 521, eluted from the column at about 19.50 minutes. Fraction AGEL 521 was prepared for spectral analysis by lyophilization from the eluent followed by lyophilization from water, according to standard methods. The lyophilized compound of fraction AGEL 521 was stored at about −80° C. under an argon atmosphere until used.

The structure of the compound which is comprised by fraction AGEL 521 was then determined by the use of FAB MS. The data so obtained and the structure deduced therefrom are as follows:

AGEL 521:

FAB MS: (high resolution) observed (M+H) M/Z=522.3774 calculated for $C_{26}H_{48}N_7O_4$ (Req 522.3768)

Structure: 1H-Indole-3-acetamide-N-(20-amino-4,8-dihydroxy-4,8,12,17-tetraazeicos-1-yl)

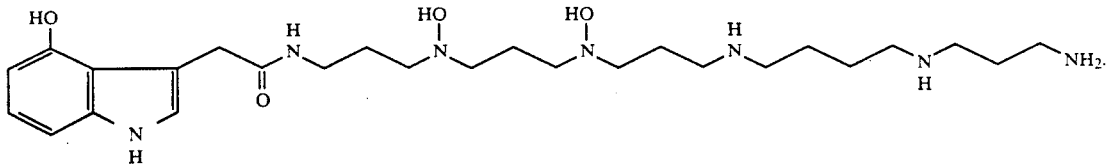

EXAMPLE 3

Subfractionation of fraction 5 and determination of the structures therein

Fraction 5, obtained as described in Example 1, was loaded onto a Dynamax Phenyl (4.6 mm×250 mm, 60 Å pore size, 8 µ particle size) column and eluted using a flow rate of 1 ml/min. and isocratic conditions of 10% B, 90% A where A and B are as described in Example 1. Peak detection and fraction collection were accomplished as described in Example 2. Fractions labelled AGEL 416 and AGEL 464 herein, were obtained as follows:

| Fraction | Elution Time |
|---|---|
| AGEL 416 | about 26.47 min. |
| AGEL 464 | about 37.76 min. |

Fractions AGEL 416 and AGEL 464 were prepared for spectral analysis and stored according to the methods described in Example 2.

The structure of the compound which is comprised by fraction AGEL 416 was determined by the use of FAB MS and the results thereof are as follows:

FAB MS: (high resolution) observed (M+H) M/Z=417.3336 calculated for $C_{23}H_{41}N_6O_4$ (Req. 417.3342)

Structure: 1H-Indole-3-acetamide-N-(16-amino-4,8,13-triazahexadec-1-yl)

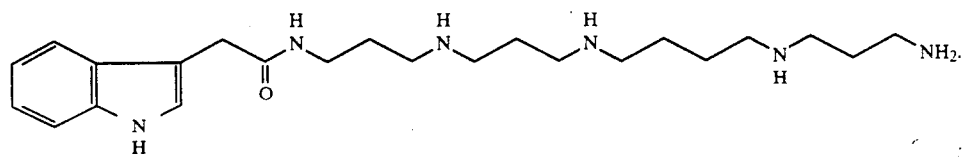

The structure of the compound which is comprised by fraction AGEL 464 was determined by the use of FAB MS and the results thereof are as follows:

FAB MS: (high resolution) observed (M+H) M/Z=465.3173 calculated for $C_{23}H_{41}N_6O_4$ for (Req. 465.3189)

Structure: 1H-Indole-3-acetamide-N-(16-amino-4,8-dihydroxy-4,8,13,-triazahexadec-1-yl)-4-hydroxy

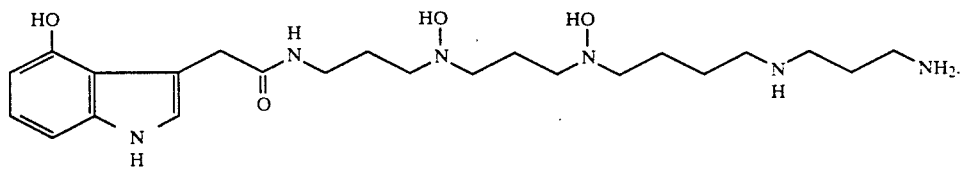

EXAMPLE 4

Subfractionation of fraction 6 and determination of the structures therein

Fraction 6, obtained as described in Example 1, was loaded onto a Dynamax Phenyl column and eluted according to the methods described in Example 3. Peak detection and fraction collection were accomplished as described in Example 2. Fractions labelled AGEL 489(A) and AGEL 489 herein, were obtained as follows:

| Fraction | Elution Time |
| --- | --- |
| AGEL 489 | about 41.95 min. |
| AGEL 489(A) | about 55.27 min. |

Fractions AGEL 489(A) and AGEL 489 were prepared for spectral analysis and stored according to the methods described in Example 2.

The structure of the compound which is comprised by fraction AGEL 489(A) was determined by the use of FAB MS and the results thereof are as follows:

FAB MS: (high resolution) observed (M+H) M/Z=489.3896 calculated for $C_{27}H_{49}N_6O_2$ (Req. 489.3917)

Structure 1H-Indole-3-acetamide-N-(17-trimethylamino-4-hydroxy-4,8,12-triazaheptadec-1-yl)

The structure of the compound which is comprised by fraction AGEL 489 was determined by the use of FAB MS and found to be the compound AGEL 489 described in U.S. application Ser. No. 07/346,181. AGEL 489 forms no part of the instant invention.

EXAMPLE 5

1H-Indole-3-acetamide-N-(16-amino-4,8,13-triazahexadec-1-yl

Synthesis of the title compound, ascertained to be comprised by fraction AGEL 416 as described in Example 3, was accomplished as described below.

The compound of formula I was prepared from diaminobutane and acrylonitrile according to the published procedure of Yamamoto, Hisashi, J. Am. Chem. Soc. 103:6133–6136 (1981).

Under nitrogen atmosphere, 5.78 g (0.041 mole) of compound of formula I, prepared as described in part A above, was added to 75 ml of CH$_3$CN and 11.48 g of KF Celite and stirred. To the stirring mixture was added a solution of 9.75 g (0.041 mole) of compound of formula II, prepared as described in Preparation A, in 25 ml of CH$_3$CN. The reaction was heated to reflux for six hours then cooled to room temperature and allowed to stand overnight. The KF-Celite was then filtered off and the filter-cake was washed well with CH$_3$CN. The filtrate was concentrated in vacuo to yield 14 g of crude product as an oil. The crude product was chromatographed on 400 g silica gel using 500 ml dichloromethane, then 1 liter of 85:15 CH$_2$Cl$_2$/MeOH followed by 1 liter of 75:25 CH$_2$Cl$_2$MeOH followed by 1 liter of 75:25 CH$_2$Cl$_2$/MeOH plus 25 ml of isopropylamine, then 1 liter of 75:25 CH$_2$Cl$_2$/MeOH plus 50 ml of isopropylamine, then 400 ml of 75:25 CH$_2$Cl$_2$/MeOH plus 75 ml of isopropylamine The fractions were monitored by thin layer chromatography and the fractions containing the desired product, confirmed by NMR, were pooled and concentrated in vacuo to yield 4.7 g of product of formula III above.

-continued

BOC−NH−N(BOC)−N(BOC)−N(BOC)−CH₂CH₂CN (IV)

Under nitrogen atmosphere, 4.7 g (15.8 mmoles) of compound of formula III, prepared as described in part B, above, was dissolved in 150 ml of dichloromethane. Then, 7,56 g (34.7 mmoles) of di-t-butyldicarbonate were added and the reaction mixture was stirred overnight at room temperature. The mixture was then concentrated in vacuo and chromatographed on 400 g of silica gel using 50:50 ethylacetate/hexane solvent. The fractions were monitored by TLC (50:50 ethylacetate/hexane). The fractions containing the product of formula IV were combined and concentrated in vacuo to yield 7.9 g of product as an oil.

(IV) D.

↓

(V)

To 125 ml of acetic acid under a nitrogen atmosphere were added 7.85 g (15.8 mmoles) of compound of formula IV, prepared as described in part C, above, and 6.5 g of Pd(OH₂)/carbon. The mixture was hydrogenated at 50 p.s.i. for 2 hours The catalyst was removed by filtration and the filter cake was washed well with acetic acid. The filtrate was concentrated, taken up in 250 ml dichloromethane, washed twice with 100 ml of 1N NaOH and dried over K₂CO₃. The solution was filtered and the filtrate was concentrated in vacuo to yield 7.8 g of compound of formula V.

V + NC⌒ ⟶   E.

(VI)

Under nitrogen atmosphere, 7.15 (14.2 mmoles) of compound of formula V, prepared as described in part D, above, was dissolved in 150 ml of methanol. Then, 1.03 ml (15.6 mmoles) of acrylonitrile was added and the reaction was stirred 72 hours at room temperature. The reaction mixture was then concentrated, reconcentrated three times from dichloromethane and stripped of solvent in vacuo to yield 7.65 g of product of formula VI as an oil.

VI + [BOC]₂O ⟶   F.

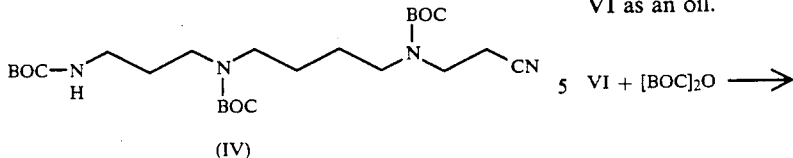

(VII)

Under nitrogen atmosphere, 6.45 g (11.6 mmoles) of compound of formula VI, prepared as described in part E, above, was dissolved in 125 ml of dichloromethane. To that solution were added 2.6 g (12 mmoles) of di-t-butyldicarbonate and the reaction stirred overnight at room temperature. The reaction mixture was then concentrated and chromatographed on 400 g silica gel using 50:50 ethylacetate/hexane as eluent. The product fractions were combined and concentrated to yield 6.6 g of product of formula VIII as an oil.

VII ⟶   G.

(VIII)

To 150 ml of acetic acid under a nitrogen atmosphere were added 6.6 g (10.1 mmoles) of compound of formula VII, prepared as described in part F, above, and 6 g of Pd(OH)₂/carbon. The mixture was hydrogenated at 50 p.s.i. for 2 hours The catalyst was removed by filtration and the filter cake was washed well with acetic acid. The filtrate was concentrated, taken up in 200 ml dichloromethane, washed twice with 100 ml 1N NaOH and dried over K₂CO₃. The solution was filtered and the filtrate was concentrated in vacuo to yield 6.5 g of product of formula VIII.

H.

indole-CH₂-COOH + HON(succinimide)

↓

(IX)

Under nitrogen atmosphere, 1.75 g (10 mmoles) of indole acetic acid, 1.15 g (10 mmoles) of N-hydroxysuccinimide and 2.06 g (10 mmoles) of dicyclohexylcarbodiimide were added to 75 ml of tetrahydrofuran. The reaction mixture was stirred at room temperature and a precipitate formed after about 5 minutes. After about 1.5 hours, the precipitate was removed by filtration, the filter cake was washed with 75 ml of tetrahydrofuran and the cake was air dried to yield 1.84 g. The combined thylamino)pyridine. The reaction was stirred at room temperature for 1 hour then allowed to stand overnight. The reaction mixture was chromatographed on silica gel using 4:1 ethylacetate/hexane and the product fractions were concentrated to yield 0.32 g of product of formula XI as a white foam.

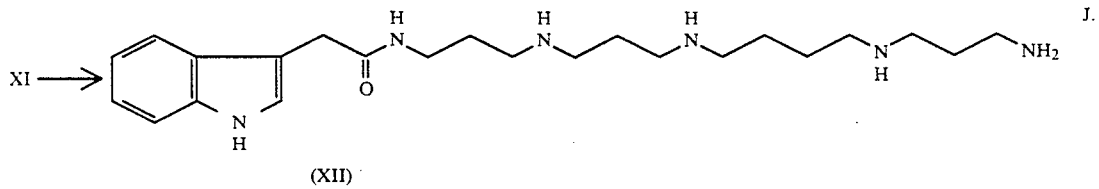

(XII)

filtrate was concentrated, taken up in ethylacetate and filtered, washing the filter with ethylacetate The filtrate was concentrated to yield a foam. The foam was triturated with 75 ml of diethylether to yield a hard gum. Then, about 30 ml of ethylacetate was added followed by ethyl ether. The solids were isolated by filtration, washed with diethyl ether and dried under nitrogen to yield 1.74 g of product of formula IX. It was found that an additional 0.47 g of product could be obtained by treating the mother liquor with petroleum ether.

Under nitrogen atmosphere, 0.32 g (0.35 mmoles) of compound of formula XI, prepared as described in part J, above, were added to 15 ml of trifluoroacetic acid and stirred for 15 minutes. The reaction mixture was then concentrated in vacuo and triturated with diethylether to yield 0.30 g of product as a white powder.

PREPARATION A

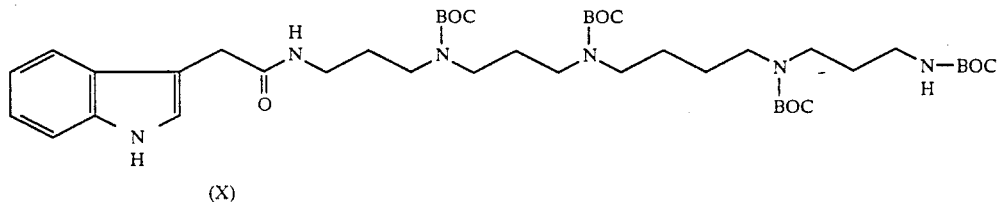

(X)

Under nitrogen atmosphere, 0.33 g (5 mmoles) of compound of formula VIII, prepared as described in part G, above, was dissolved in 10 ml of dichloromethane with stirring and then 0.136 g (5 mmoles) of compound of formula IX, prepared as described in part H, above, were added. The reaction was stirred overnight at room temperature. The reaction mixture was then diluted out to 35 ml with dichloromethane, washed with 10 ml of 0.5N NaOH, dried over $K_2CO_3$, and concentrated. The concentrate was chromatographed on silica gel using 4:1 ethylacetate/hexane. The product fractions were concentrated to yield 0.37 g of a white foam containing product of formula X with some ethylacetate present.

Under nitrogen atmosphere, 34.5 g (157.6 mmoles) of 3-bromopropylamine HBr in 600 ml of N,N-dimethylformamide was stirred. To that solution was added 34.4 g (157.6 mmoles) of di-t-butyldicarbonate followed by 32.3 ml (236 mmoles) triethylamine. A precipitate formed immediately. The reaction was stirred overnight. The reaction mixture was then diluted to 1.5 liters with ethylacetate, washed once with 500 ml of 1N HCl, three times with 500 ml water, once with brine and dried over $Na_2SO_4$. After concentration, the product was chromatographed on 800 g silica gel using 4:1 hexane/ethylacetate and the fractions were monitored by TLC ($KMNO_4/I_2$) The fractions containing the product were combined, concentrated in vacuo, chased twice

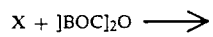

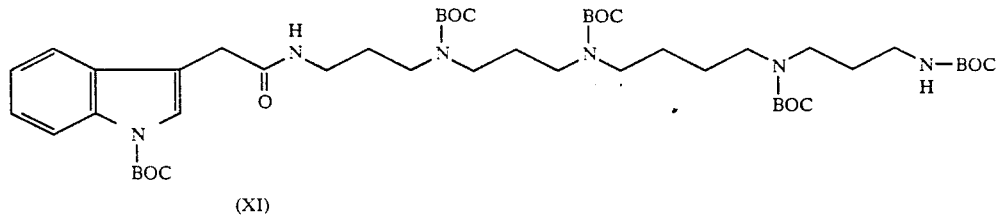

(XI)

Under nitrogen atmosphere, 0.37 g (0.45 mmoles) of compound of formula X, prepared as described in part I, above, was dissolved in 10 ml of dichloromethane. Then 0.218 g (1 mmole) of di-t-butyldicarbonate were added followed by 12 ml (0.1 mmole) of 4-(N,N-dimewith 50 ml dichloromethane and purged with high vacuum to yield 25.8 g of the product of this Preparation.

What is claimed is:

1. A substantially pure compound of the formula

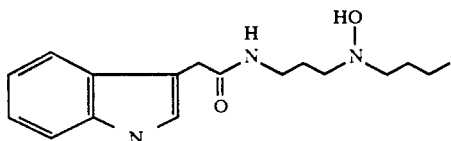

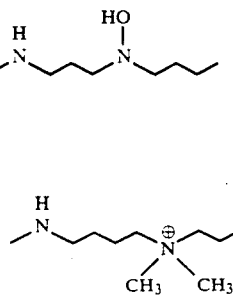

and the pharmaceutically-acceptable salts thereof.

2. A substantially pure compound of the formula

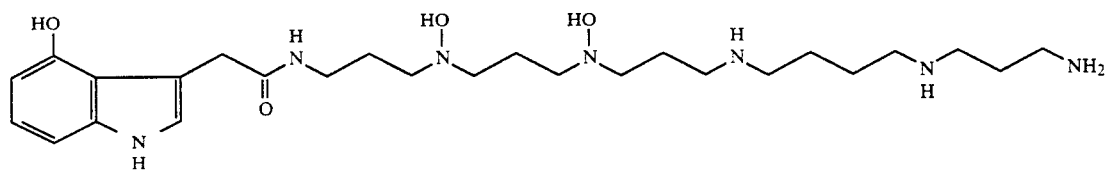

and the pharmaceutically-acceptable salts thereof.

3. A substantially pure compound of the formula

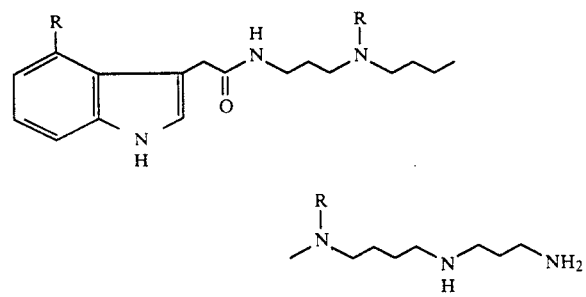

and the pharmaceutically-acceptable salts thereof wherein each R is the same and is H or OH.

4. The compound or a pharmaceutically-acceptable salt thereof according to claim 3 wherein R is H.

5. The compound or a pharmaceutically-acceptable salt thereof according to claim 3 wherein R is OH.

6. A method of antagonizing an excitatory amino acid neurotransmitter, which neurotransmitter affects a cell, said method comprising administering to said cell an excitatory amino acid neurotransmitter antagonizing amount of a compound according to claim 1 or a pharmaceutically-acceptable salt thereof.

7. The method according to claim 6 wherein the cell is in the nervous system of a mammal.

8. The method according to claim 6 wherein the cell is in the nervous system of an invertebrate.

9. A method of antagonizing an excitatory amino acid neurotransmitter, which neurotransmitter affects a cell, said method comprising administering to said cell an excitatory amino acid neurotransmitter antagonizing amount of a compound according to claim 2 or a pharmaceutically-acceptable salt thereof.

10. The method according to claim 9 wherein the cell is in the nervous system of a mammal.

11. The method according to claim 9 wherein the cell is in the nervous system of an invertebrate.

12. A method of antagonizing an excitatory amino acid neurotransmitter, which neurotransmitter affects a cell, said method comprising administering to said cell an excitatory amino acid neurotransmitter antagonizing amount of a compound according to claim 4 or a pharmaceutically-acceptable salt thereof.

13. The method according to claim 12 wherein the cell is in the nervous system of a mammal.

14. The method according to claim 12 wherein the cell is in the nervous system of an invertebrate.

15. A method of antagonizing an excitatory amino acid neurotransmitter, which neurotransmitter affects a cell, said method comprising administering to said cell an excitatory amino acid neurotransmitter antagonizing amount of a compound according to claim 5 or a pharmaceutically-acceptable salt thereof.

16. The method according to claim 15 wherein the cell is in the nervous system of a mammal.

17. The method according to claim 15 wherein the cell is in the nervous system of an invertebrate.

18. A pharmaceutical composition for antagonizing an excitatory amino acid neurotransmitter, which neurotransmitter affects a cell in the nervous system of a mammal, said composition comprising an excitatory amino acid neurotransmitter antagonizing amount of a compound according to claim 1 or a pharmaceutically-acceptable salt thereof and a pharmaceutically-acceptable diluent or carrier.

19. A pharmaceutical composition for antagonizing an excitatory amino acid neurotransmitter, which neurotransmitter affects a cell in the nervous system of a mammal, said composition comprising an excitatory amino acid neurotransmitter antagonizing amount of a compound according to claim 2 or a pharmaceutically-acceptable salt thereof and a pharmaceutically-acceptable diluent or carrier.

20. A pharmaceutical composition for antagonizing an excitatory amino acid neurotransmitter, which neurotransmitter affects a cell in the nervous system of a mammal, said composition comprising an excitatory amino acid neurotransmitter antagonizing amount of a compound according to claim 4 or a pharmaceutically-acceptable salt thereof and a pharmaceutically-acceptable diluent or carrier.

21. A pharmaceutical composition for antagonizing an excitatory amino acid neurotransmitter, which neurotransmitter affects a cell in the nervous system of a mammal, said composition comprising an excitatory amino acid neurotransmitter antagonizing amount of a compound according to claim 5 or a pharmaceutically-acceptable salt thereof and a pharmaceutically-acceptable diluent or carrier.

* * * * *

UNITED STATES PATENT AND TRADEMARK OFFICE
CERTIFICATE OF CORRECTION

PATENT NO. : 5,037,846
DATED : August 6, 1991
INVENTOR(S) : Saccomano et al.

It is certified that error appears in the above-identified patent and that said Letters Patent is hereby corrected as shown below:

Title page, the Assignee should include Natural Product Sciences, Inc., Salt Lake City, Utah, in addition to Pfizer Inc.

Column 3, line 45, "250 pore size" should read --250 mm--.

Column 20, line 67, "$KMN_{04}$" should read --$KMNO_4$--.

Col. 21;
In claim 1, line 15,

" 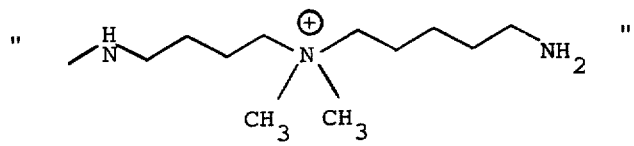 "

should read

-- 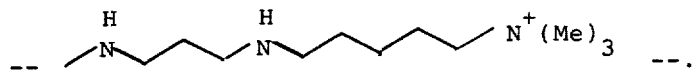 --.

Signed and Sealed this

Ninth Day of February, 1993

Attest:

STEPHEN G. KUNIN

Attesting Officer

Acting Commissioner of Patents and Trademarks